(12) United States Patent
Jimenez et al.

(10) Patent No.: US 12,308,114 B2
(45) Date of Patent: May 20, 2025

(54) SYSTEM AND METHOD FOR EMERGENCY MEDICAL EVENT CAPTURE, RECORDING AND ANALYSIS WITH GESTURE, VOICE AND GRAPHICAL INTERFACES

(71) Applicant: CodeScribe Corporation, Austin, TX (US)

(72) Inventors: Ronald W. Jimenez, San Jose, CA (US); Che-Chuen Ho, Santa Clara, CA (US); William Conrad Altmann, Austin, TX (US)

(73) Assignee: CodeScribe Corporation, Austin, TX (US)

( * ) Notice: Subject to any disclaimer, the term of this patent is extended or adjusted under 35 U.S.C. 154(b) by 428 days.

(21) Appl. No.: 17/364,568

(22) Filed: Jun. 30, 2021

(65) Prior Publication Data
US 2022/0044793 A1     Feb. 10, 2022

Related U.S. Application Data

(60) Provisional application No. 63/061,618, filed on Aug. 5, 2020.

(51) Int. Cl.
*G16H 40/20*     (2018.01)
*G06F 3/04817*     (2022.01)
(Continued)

(52) U.S. Cl.
CPC ......... *G16H 40/20* (2018.01); *G06F 3/04817* (2013.01); *G06F 3/0486* (2013.01);
(Continued)

(58) Field of Classification Search
CPC ........ G16H 40/20; G16H 40/67; G16H 10/60; G16H 50/70; G16H 50/20; G16H 70/20
See application file for complete search history.

(56) References Cited

U.S. PATENT DOCUMENTS 10,198,967 B1    2/2019   Agrawal et al.
10,895,906 B2    1/2021   West et al.
(Continued)

OTHER PUBLICATIONS

Drag and drop, Wikipedia, Jul. 15, 2019, https://en.wikipedia.org/w/index.php?title=Drag_and_drop&oldid=906389830 (Year: 2019).*

(Continued)

*Primary Examiner* — Joshua B Blanchette
(74) *Attorney, Agent, or Firm* — Perkins Coie LLP

(57) ABSTRACT

Introduced here are approaches for capturing and recording medical event details during cardiopulmonary resuscitation (CPR) events and other emergency medical events. A recording begins when an operator inputs a request to initiate recording. The operator may use a recording system with a combination of input devices to record medical actions. The recording system acknowledges the operator's actions by various means which may include icons displayed for the operator. The operator's interactions with the icons indicate corresponding actions observed by the operator, which are recorded as a log of the actions in temporal order that serves as a non-transient record of the medical event. An analysis of the recorded details of the medical event, by comparing the actions to prescribed actions in one or more professional standards, can provide an assessment of the actions taken.

23 Claims, 14 Drawing Sheets

(51) Int. Cl.

| | | |
|---|---|---|
| *G06F 3/0486* | (2013.01) | |
| *G16H 10/60* | (2018.01) | |
| *G16H 40/67* | (2018.01) | |
| *G16H 50/20* | (2018.01) | |
| *G16H 50/70* | (2018.01) | |
| *G16H 70/20* | (2018.01) | |
| *A61H 31/00* | (2006.01) | |

(52) U.S. Cl.
CPC .............. *G16H 10/60* (2018.01); *G16H 40/67* (2018.01); *G16H 50/20* (2018.01); *G16H 50/70* (2018.01); *G16H 70/20* (2018.01); *A61H 31/004* (2013.01)

(56) References Cited

U.S. PATENT DOCUMENTS

| | | | |
|---|---|---|---|
| 11,043,137 | B2 | 6/2021 | Sweet et al. |
| 2006/0095853 | A1* | 5/2006 | Amyot .................. G16H 50/70 715/744 |
| 2007/0111174 | A1 | 5/2007 | Kozmenko et al. |
| 2008/0076100 | A1 | 3/2008 | Hendrickson et al. |
| 2008/0138778 | A1 | 6/2008 | Eggert et al. |
| 2008/0138779 | A1 | 6/2008 | Eggert et al. |
| 2009/0263775 | A1 | 10/2009 | Ullrich |
| 2012/0052470 | A1 | 3/2012 | Woerlee et al. |
| 2012/0282583 | A1 | 11/2012 | Thaler et al. |
| 2014/0011173 | A1 | 1/2014 | Tepper et al. |
| 2014/0081659 | A1 | 3/2014 | Nawana et al. |
| 2014/0127663 | A1 | 5/2014 | Eggert et al. |
| 2014/0198130 | A1 | 7/2014 | Lacroix |
| 2015/0187231 | A1 | 7/2015 | Stephanian |
| 2015/0278483 | A1* | 10/2015 | Pruitt .................... G16H 10/60 705/3 |
| 2015/0379882 | A1 | 12/2015 | Gaitán et al. |
| 2015/0379901 | A1 | 12/2015 | Welch et al. |
| 2017/0105614 | A1 | 4/2017 | Mcwilliam et al. |
| 2018/0158376 | A1 | 6/2018 | Tessier et al. |
| 2018/0261219 | A1 | 9/2018 | Brooks |
| 2019/0282324 | A1* | 9/2019 | Freeman ................. A61B 1/05 |
| 2019/0340943 | A1 | 11/2019 | Jimenez et al. |
| 2020/0202746 | A1 | 6/2020 | Olsson |
| 2020/0296147 | A1* | 9/2020 | Eliason ................. H04L 65/403 |
| 2021/0065911 | A1 | 3/2021 | Goel et al. |
| 2021/0090451 | A1* | 3/2021 | Frist, Jr. ................ G09B 23/288 |
| 2021/0295741 | A1 | 9/2021 | Bluemler et al. |
| 2022/0157418 | A1* | 5/2022 | Ashmore ............... G16H 15/00 |
| 2022/0215780 | A1 | 7/2022 | Jimenez et al. |
| 2022/0359064 | A1* | 11/2022 | Pierson ................. G16H 40/40 |

OTHER PUBLICATIONS

International Search Report mailed Jul. 10, 2019 for PCT Application No. PCT/US2019/030217; 10 pages., Jul. 10, 2019, 10 pages.
"Cyberglove Systems: CyberGrasp System User Guide v2.0, rev E", [Retrieved on Jun. 25, 2019]. Retrieved from the Internet. <https://static1.squarespace.com/static/559c381ee4b0ff7423b6b6a4/t/574f4d2a859fd0c514208 8db/1464814893851/CyberGrasp_UserGuide_2009_1.pdf>., Dec. 2007, entire document.

* cited by examiner

STANDARD REPORTING OF IN-HOSPITAL CARDIOPULMONARY RESUSCITATION

1. Date of event ☐☐ ☐☐ ☐☐
   month  day  year

2. Location
   ☐ CCU         ☐ PAR
   ☐ ICU         ☐ Operating area
   ☐ ED          ☐ General care
   ☐ Outpatient
   ☐ Diagnostic & intervention
   ☐ Other _____

3. Witnessed?
   ☐ Yes   ☐ No   ☐ Unknown
   Monitored? ☐ Yes   ☐ No

4. ACLS interventions at time of event *(check all that apply)*
   ☐ None
   ☐ IV access
   ☐ IV medications
   ☐ ECG monitor
   ☐ Intubation
   ☐ Mechanical ventilation
   ☐ Implantable defibrillator/ cardioverter
   ☐ Intra-arterial catheter Name _____
Date of birth ☐☐ ☐☐ ☐☐
   month  day  year
Age ☐☐☐
M☐   F☐   Unknown ☐
Admit date ☐☐ ☐☐ ☐☐
ID# ☐☐☐☐☐☐☐

EVENT VARIABLES

5. Immediate cause *(check one)*
   ☐ Lethal arrhythmias
   ☐ Hypotension
   ☐ Respiratory depression
   ☐ Metabolic
   ☐ MI or ischemia
   ☐ Unknown
   ☐ Other _____

6. Resuscitation attempted?
   ☐ Yes *(check all used)*
      ☐ Chest compressions
      ☐ Defibrillation
      ☐ Airway
   ☐ No *(check one)*
      ☐ Found dead
      ☐ Considered futile
      ☐ DNAR 7. Initial condition
   Conscious?  ☐ Yes  ☐ No
   Breathing?  ☐ Yes  ☐ No
   Pulse?      ☐ Yes  ☐ No 9. Event times
   *(shaded times are required to calculate the AHA and ERC in-hospital chain-of-survival intervals)*
   Collapse/Onset     ____:____
   CPR team called    ____:____
   CPR team arrived   ____:____
   Arrest confirmed   ____:____
   CPR started        ____:____  = ____ min
   1st defib shock    ____:____  = ____ min
   Airway achieved    ____:____  = ____ min
   1st dose EPI       ____:____  = ____ min 8. Initial rhythm
   ☐ VF    ☐ Bradycardia
   ☐ VT    ☐ Asystole
   ☐ PEA   ☐ Perfusing rhythm CPR stopped ____:____
   Why?
   ☐ ROSC    ☐ Futile
   ☐ Death   ☐ DNAR

*Spontaneous circulation*
   ☐ Returned *(if yes, time of ROSC)* ____:____
   ☐ Never achieved
   ☐ Unsustained ROSC:
      ☐ ≤ 20 min
      ☐ >20 min but ≤ 24 hours
      ☐ > 24 hours

OUTCOME VARIABLES

10. Time of awakening  Time ____:____  Date ☐☐ ☐☐ ☐☐

11. In-hospital event outcome *(check one)*
    ☐ Hospital discharge   Date ☐☐ ☐☐ ☐☐
       Discharge destination: other hospital ____  home ____
                              chronic care facility ____  other ____
       *CPC at discharge = ____
       *Total GCS = ____ [eye ____ verbal ____ motor ____]
    ☐ In hospital death *(ROSC>24 hours)*   Date ☐☐ ☐☐ ☐☐

12. Alive at six months?
    ☐ Yes (*CPC) = ____   ☐ No (Date of Death) ____/____/____   ☐ Unknown 13. Alive at one year?
    ☐ Yes (*CPC) = ____   ☐ No (Date of Death) ____/____/____   ☐ Unknown 14. If died, principal cause of death
    ☐ CAD      ☐ Trauma
    ☐ Cancer   ☐ Other medical 15. ICD-CM code ☐☐☐☐☐

16. Information source *(for 14 & 15)*
    ☐ Medical records
    ☐ Death certificate
    ☐ Personal physician
    ☐ Autopsy
    ☐ Other

*CPC (Cerebral Performance Category) 1 = good, 2 = moderate, 3 = severe, 4 = comatose, 5 = brain death
*GCS (Glasgow Coma Score) eye 1-4, verbal 1-5, motor 1-6.

Figure 3A

SYSTEM AND METHOD FOR EMERGENCY MEDICAL EVENT CAPTURE, RECORDING AND ANALYSIS WITH GESTURE, VOICE AND GRAPHICAL INTERFACES

CROSS-REFERENCE TO RELATED APPLICATIONS

This application claims priority to U.S. Provisional Application No. 63/061,618, titled "System and Method for Cardiopulmonary Resuscitation Event Capture, Recording and Analysis with Gesture, Voice and Graphical Interfaces" and filed on Aug. 5, 2020, which is incorporated by reference herein in its entirety.

TECHNICAL FIELD

The present disclosure relates to systems and methods for capturing and recording medical event details during cardiopulmonary resuscitation (CPR) events and other emergency medical events.

BACKGROUND

Present systems and methods capture details during CPR events manually using non-standardized paper and ordinary paper and frequently complete the details at the termination of CPR. This process can contribute to errors including incomplete data, and poor correlation across events.

BRIEF DESCRIPTION OF THE DRAWINGS

FIG. 3A is an example of a form that would have historically been used to record information regarding events.

DETAILED DESCRIPTION

In the area of CPR events and emergency trauma events, standards provide direction to be used in such events, and it is the details of an event which are captured, recorded and compared to the prescribed standards. However the formats of these recorded documents are not standardized, which creates inefficiencies and can contribute to errors in transcription. Examples of such protocols include Advanced Cardiac Life Support (ACLS), Pediatric Advanced Life Support (PALS), and Neonatal Advanced Life Support (NALS) from the American Heart Association; and Advanced Trauma Life Support (ATLS), from the American College of Surgeons.

CPR events are customarily referred to as "Code Blue events," and the terms may be used interchangeably in this context. Note that while embodiments may be described in the context of CPR events, those skilled in the art will recognize that the technology is similarly applicable to other emergency medical events.

Overview of Recording System

Figure 1:
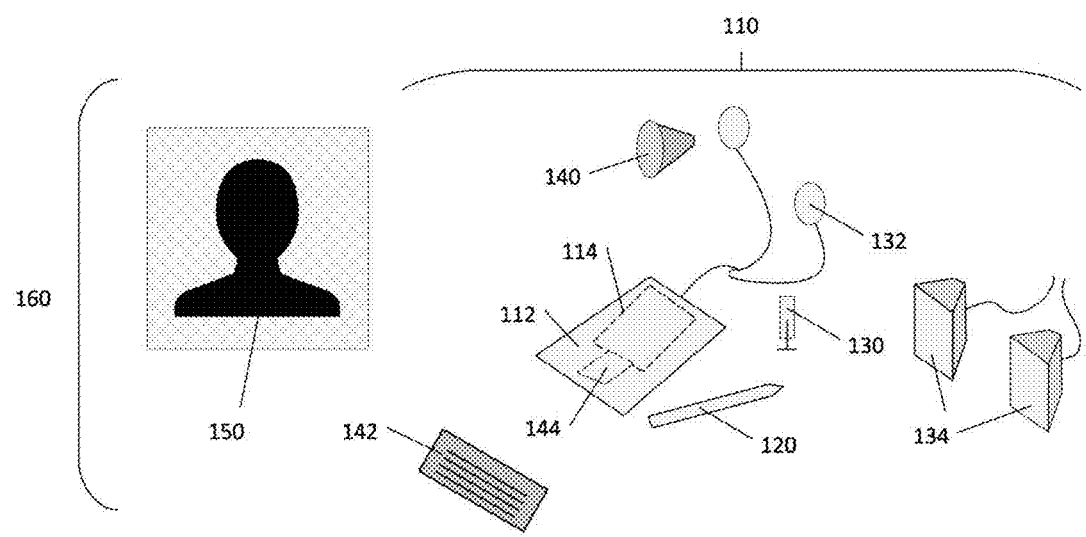
FIG. 1 is a depiction of a recording system in accordance with embodiments of the present disclosure.

FIG. 1 is an illustration of a Recording System 100 that comprises a Recording Device 110, including a Display Screen 112 with Touch Screen 114; a Recording Stylus 120; a Recording Microphone 130; a Headset 132; Speakers 134; a Camera 140; a Keyboard 142; a Touchpad 144; and a Location System 146. Embodiments of the Recording System 100 may include some or all of these components, as well as components not shown in FIG. 1. Also shown is an Operator 150, who is positioned in the CPR Event Space 160.

FIG. 2A through FIG. 2E illustrate a Recording User Interface 200. The Operator 150 may be able to interact with the Recording User Interface 200 on the Recording System 100 using icons, drag-and-drop, or selecting from fixed content on drop-down lists, to record each action during the course of the event in the CPR Event Space 160.

FIG. 3A is an illustration of a form used to record events (Circulation, Vol. 95, No. 8; American Heart Association, 1997).

Figure 3B:
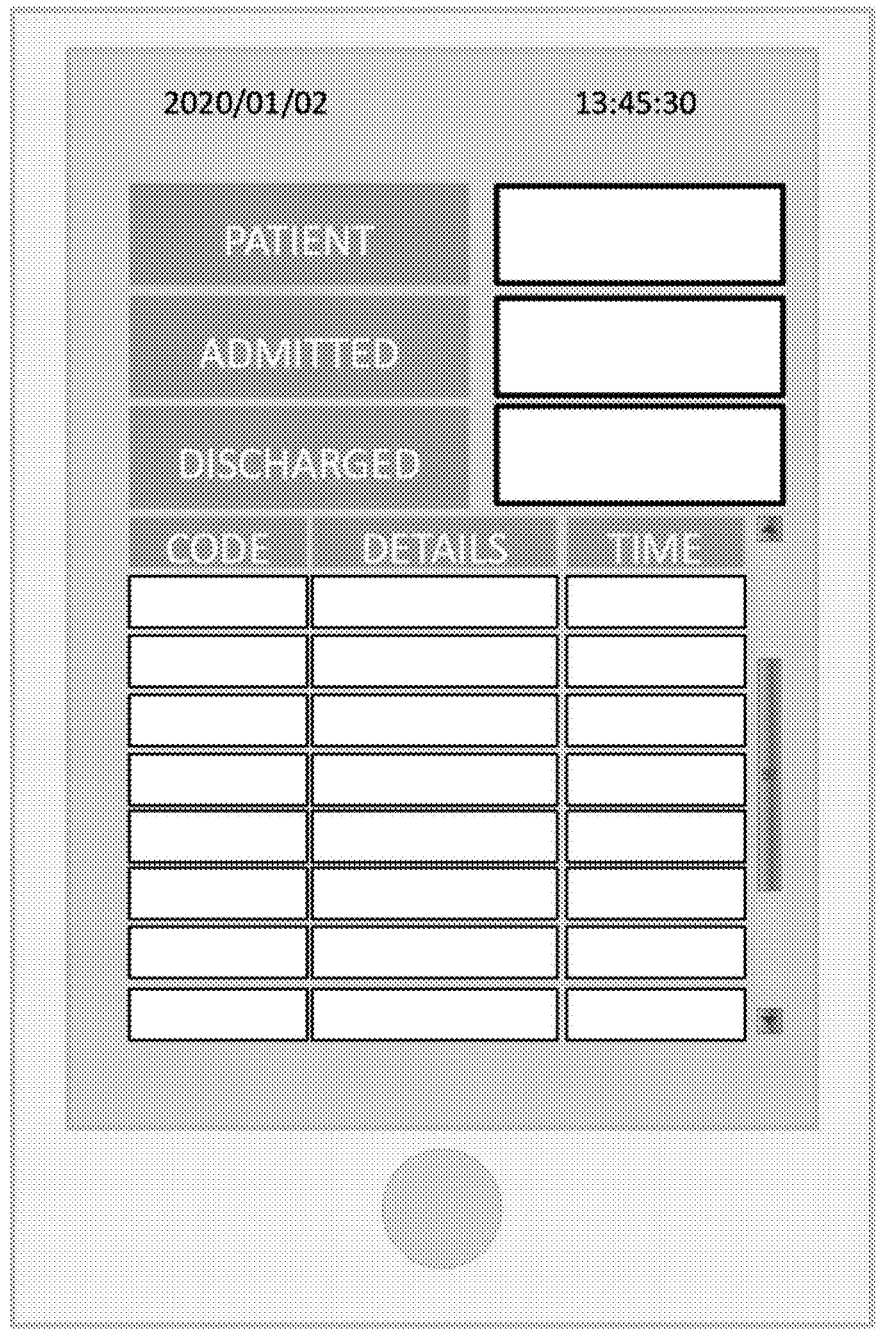
FIG. 3B is a text-based application that may be used to record events.

FIG. 3B is an illustration of a text-based application used to record events.

Figure 4:
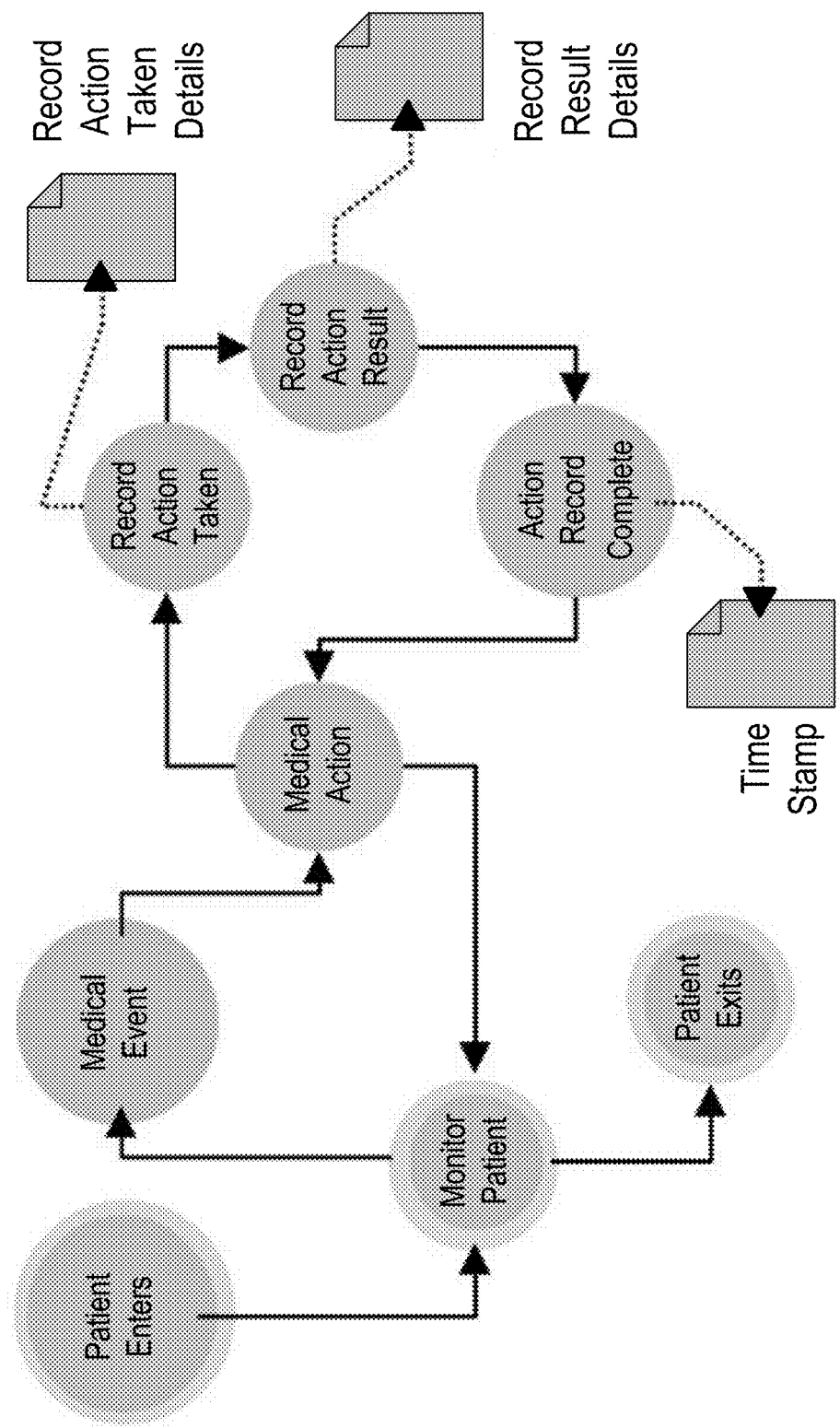
FIG. 4 is a flowchart of a process for using the system.

FIG. 4 is a flowchart of the process of Operator 150 input to the Recording System 100, beginning with a CPR Event 410; proceeding to Medical Action 420; then Record Action 430; then Record Action Taken Details 432; then Confirm Action Recorded 434; then Record Action Result 440; then Record Action Result Details 442, then Confirm Results Recorded 444, then Medical Action Complete 450 with a Time Stamp 452; repeating through a series of Medical Actions, from the Patient Entering 460, during Monitoring the Patient 462, until the Patient Exits 464.

Recording System

The Operator 150 uses a Recording System 100 with a combination of input devices to record Medical Actions 420 as they occur during the CPR Event 410. The Recording System acknowledges the Operator's actions by various means which may include a plurality of icons displayed for the Operator.

The Operator 150 may use one or more of the Touch Screen 114, the Recording Stylus 120, the Recording Microphone 130, the Camera 140, the Keyboard 142 and the Touchpad 144 to input Medical Actions 420. The Recording System 100 may use one or more of the Display Screen 112, the Headset 132 and the Speakers 134 to indicate to the Operator that the input Medical Action has been accepted or not accepted into the system.

In an example, the Recording System 100 may be one or more of a smart phone, a tablet, a laptop computer. The Recording System allows the Operator 150 to be mobile while also recording information.

As diagrammed in FIG. 4, the Patient enters the CPR Event Space 160 and is monitored during the sequence of Medical Actions 420 until the Patient exits the CPR Event Space. At each Medical Action, an action is taken by one or more healthcare professionals and the Medical Action is recorded by the Operator 150 into the Recording System 100. The Operator records the action and the action's result. The Recording System records the completion of each action, including a timestamp for the completion. The process of recording actions and timestamps is repeated for each action during the course of attending to the Patient. Thus, the Recording System 100 may populate, for each input provided by the Operator 150, an entry in a data structure with information regarding (i) a type of action performed, (ii) a healthcare professional who performed the action, and/or (iii) a time at which the action was performed.

In an example, healthcare professionals encompass medical doctors, nurses, paramedics, emergency medical technicians, military medical personnel.

In an example, the Operator 150 may record the action when requested by the personnel, then the performing of the action, then the completion of the action, each step in an action with the corresponding interaction with the Recording User Interface 200. This process is shown in FIG. 4.

In an example, the Recording System 100 may record into the Log 260 a Time Stamp 452, with the time indicated at the level of day, hour, minute and second.

In an example, the Operator 150 uses a Touch Screen 114 to select icons. The Recording System 100 responds by modifying the format of the selected icon, using multiple formats for the icon, such as one for a successful icon selection and a distinct format for an unsuccessful icon selection attempt.

The Operator 150 proceeds to record each action during the CPR Event 410.

The Operator 150 may record into the Recording System 100 the arrival and departure of each healthcare professional involved in the emergency medical event, including the beginning and end of each specific Operator's use of the Recording System as the Recording System may be passed from one Operator to another Operator during the course of the emergency medical event.

In an example, the Recording System 100 recognizes the arrival and departure of each of a plurality of medical professionals using data from a badge worn by the person.

Limitations in Capturing Event Data

FIG. 3A illustrates an example of a text form, used to capture event details. The operator using this form is not prompted to enter information, nor assisted on the form in showing options which may be entered into a specific field on the form. The operator must initiate a new form for each event, or use limited space when a sequence of actions is to be recorded in a tabular manner on a consolidated form.

FIG. 3B illustrates an example of a tablet-based application which uses text entry fields to record event details. Studies have shown that textual data entry user interfaces limit the efficiency of the operator when compared to icon-based user interfaces.

Icon-Based, Drag-and-Drop Application

FIG. 2A through FIG. 2E illustrate an example of the Recording User Interface 200. In this application, the primary user interface modality is the use of icons. The Operator 150 is presented with a set of Icons 220 on the Desktop 202 which cover all of the possible Medical Actions which the Operator may be called on to record during the CPR event.

Icons 220 or drop-down menus may be presented to the Operator 150 at levels below that of the Desktop 202, based upon previous selection actions by the Operator. Only those icons related to actions previously performed by the Operator may be presented in unmodified form on the interface.

Icons 220 or drop-down menus may be presented to show the status of the software system, not to show the medical status of the code, patient or event in progress.

In an example, icons not pertinent to the currently-selected operation are changed in color to a less noticeable color such as grey, this change indicating to the user that the icon is not related to the action they have opened by a prior screen action.

In an example, an icon which has been selected to initiate an action may itself be modified according to the state of the action, such as 'pending', 'ongoing', 'incomplete', this modification may be a change in icon color, change in the icon to include a textual label indicating the state, an added digital badge indicating the state, or a change in the icon image, the change made to inform the user.

In an example, a green dot is added as a badge on an icon to indicate an icon in active use, a blue dot to indicate an icon waiting to be activated, a red asterisk to indicate a fault with the equipment associated with the icon, a black checkmark to indicate completion of use of the equipment or process associated with the icon.

In an example, an opaque icon is used to indicate active use of the associated equipment or process, a partially transparent icon to indicate pending use, and a monochrome icon to indicate that that icon is not selectable.

Figure 2A:
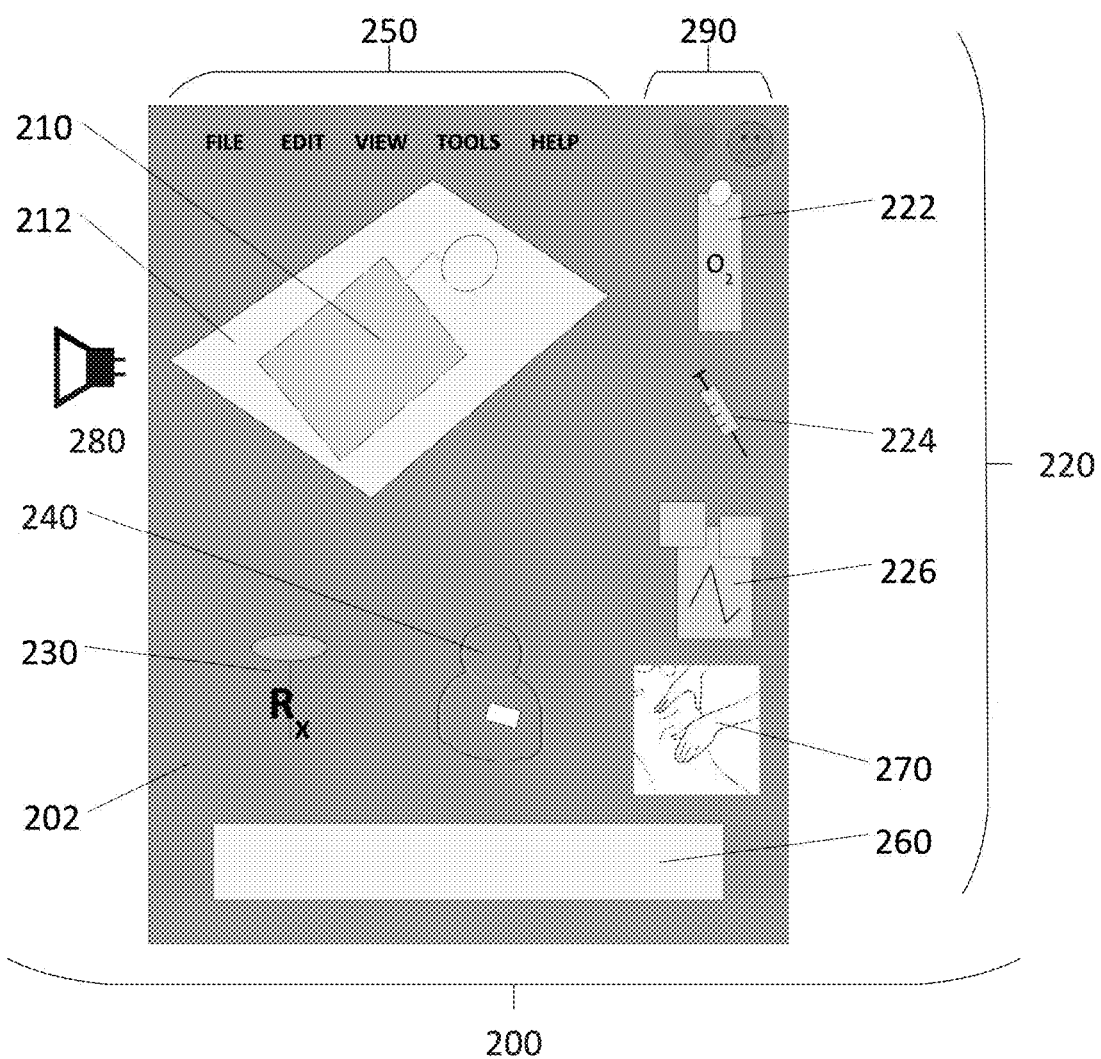
FIG. 2A through FIG. 2E depict examples of user interfaces that may be displayed by the recording system.

FIG. 2A illustrates an example set of user interface elements. A set of one or more Equipment Icons 220 is presented to the Operator 150. The Operator selects one Equipment Icon at a time, corresponding to the action observed during the CPR Event 510. A Medication Icon 230 is presented when needed to record details about each medication or treatment delivered. A Personnel Icon 240 is presented to select the one or more personnel involved in the action, each Personnel Icon representing the role assigned to one person. A Toolbar 250 may be included in the user interface for use when the Operator is not actively recording actions. A Log 260 may be included in the user interface as a visual confirmation of the events and details recorded by the Operator, including the profile details for the Operator.

Medication Icons 230 encompass actions including delivery of medication, activation of equipment, delivery of treatments directly by personnel and the like.

The Log 160 may be copied to the Recording System 100 or another computing device as a non-transient record of the entire CPR Event 510. For example, the Log 160 may be stored in the memory of the Recording System 100, or the Log 160 may be stored in a memory that is accessible to the Recording System 100 (e.g., via a network).

Equipment Selection

Figure 2B:
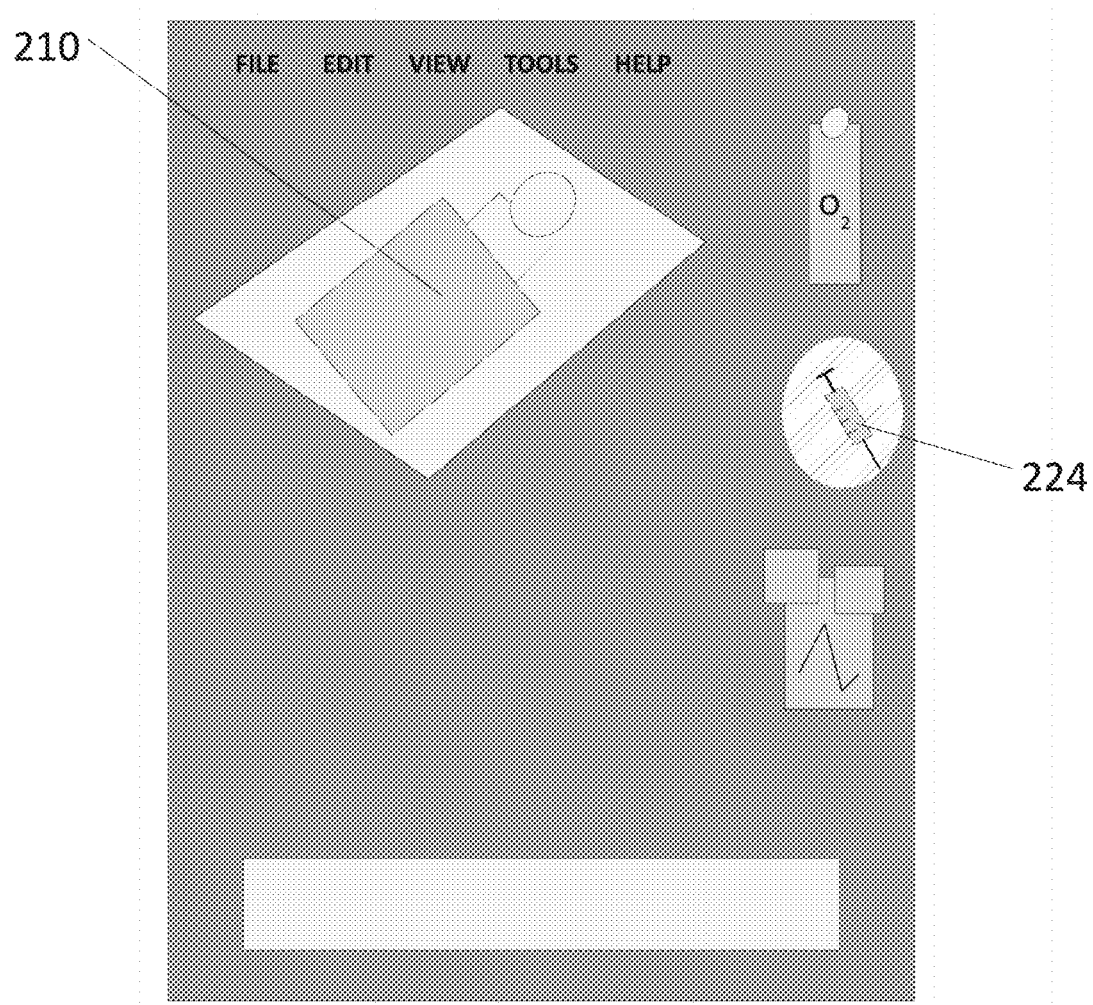

FIG. 2B illustrates an example of use of the Recording User Interface 200 for one Medical Action 520. When the Operator sees one of the personnel using a needle to deliver medication to the Patient, the Operator selects from among the Equipment Icons 220, and moves the Injection Icon 224 over the location on the Patient Icon 210 corresponding to the action at that time during the event.

In an example, specific equipment is represented by the Oxygen Icon 222 and the Defibrillator Icon 226.

In an example, the interface provides unique copies of icons according to the number of real items in the event. For example, the Injection Icon 224 is replicated as many times as needed to provide delivery of medication, each time using a copy of the Injection Icon to drag onto the Patient Icon 210. For example, in an event with one defibrillator unit present, the Defibrillator Icon 246 has only one instance in the interface.

In an example, the interface provides one icon for each type of equipment, the icons being visually understood by the medical professionals in the CPR Event Space 160, and reacts to selection of one of Equipment Icon 220 by displaying an indicator of the number of units of that type of equipment available in the CPR Event Space. For example, the Oxygen Icon 222 is shown once on the interface, but when selected shows the number of oxygen tanks available.

Figure 2C:
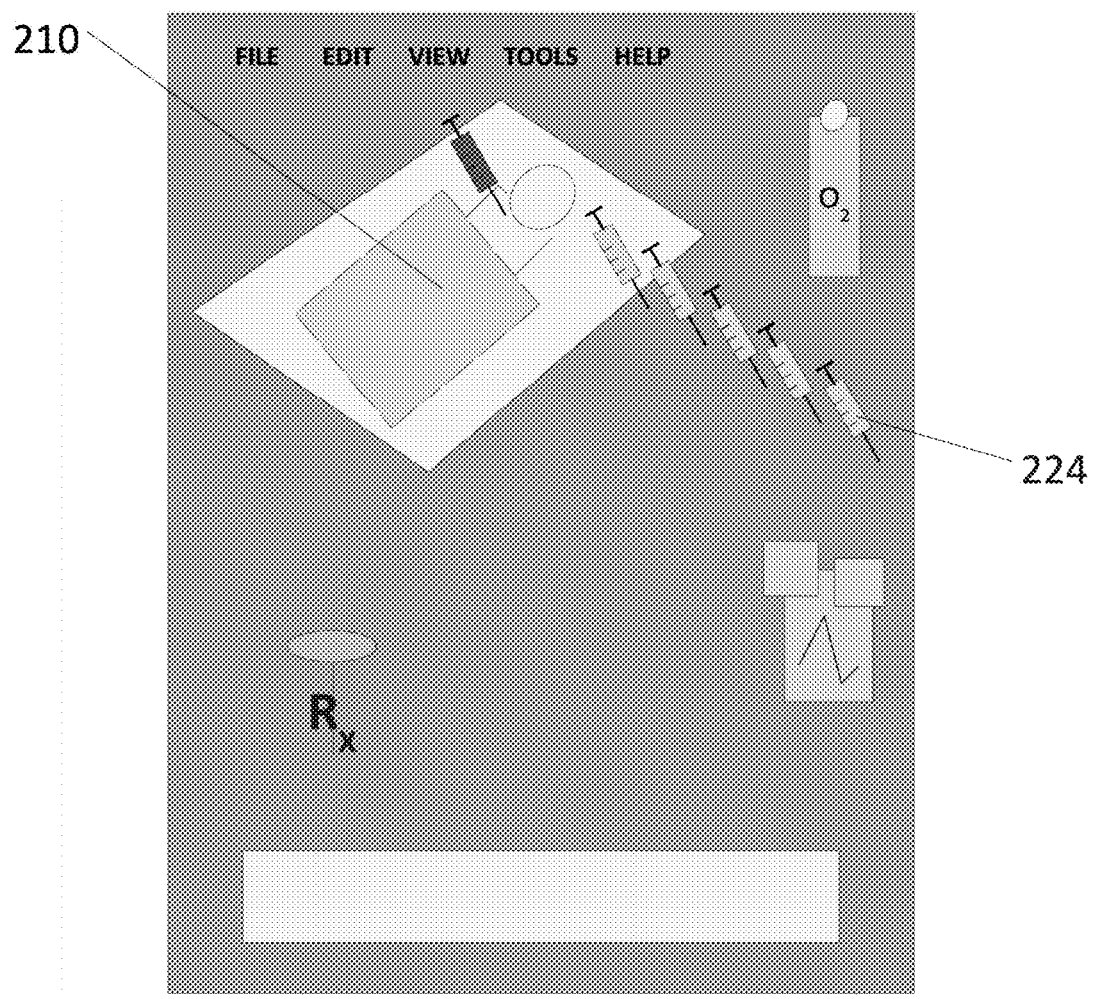
Figure 2D:
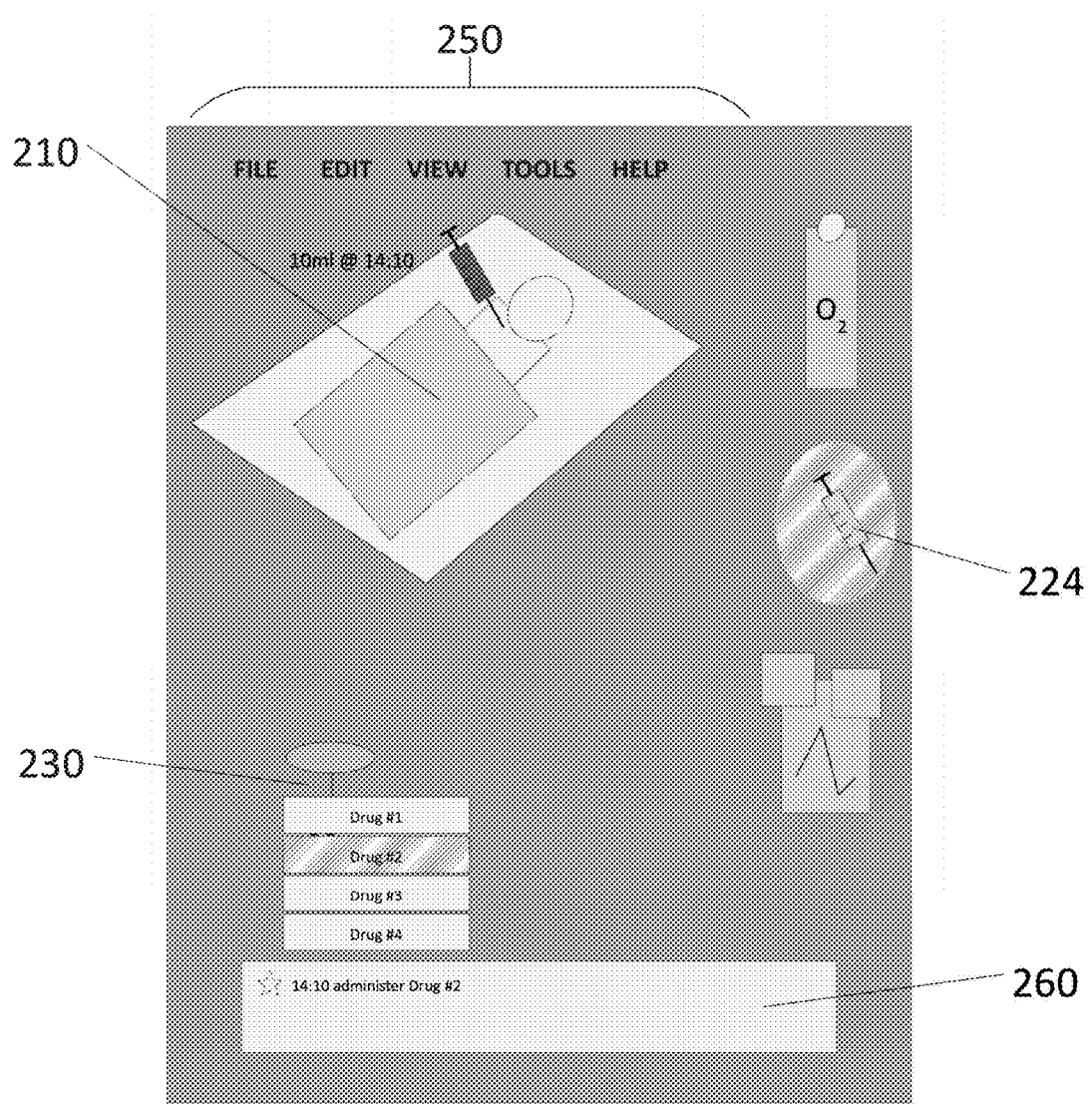
Figure 2E:
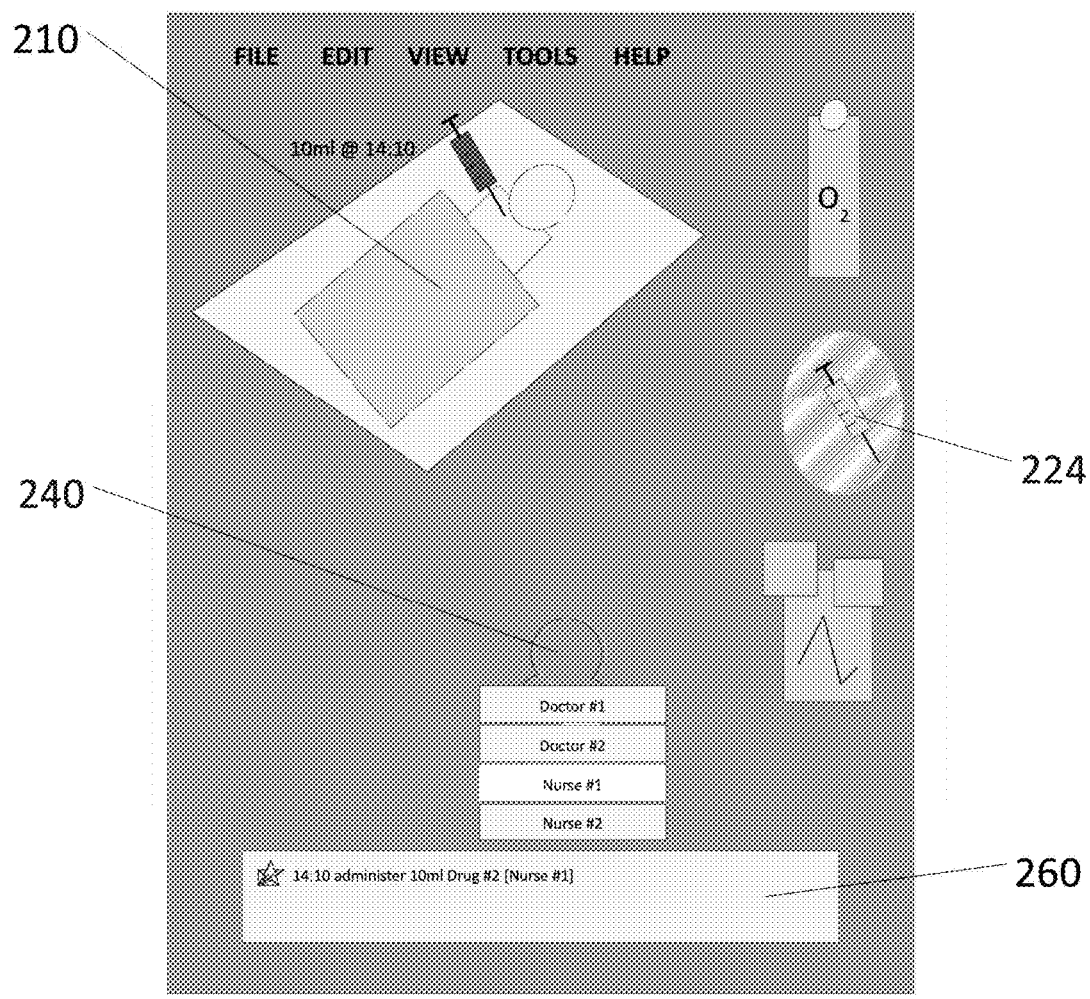

In FIG. 2C, the Operator drags a copy of the Injection Icon 244 to the relative position on the Patient Icon 210 in the interface, such as the arm. The dragged Injection Icon is released when dropped on the Patient Icon to indicate the beginning of injection of the medication.

In an example, the Injection Icon 244 is marked in a distinctive manner, such as change of color or shading or transparency, to indicate it is actively delivering medication.

In an example, the Oxygen Icon 222, after being put in use with the patient, has a changing appearance according to the remaining oxygen in the tank, such as changing the color of one portion of the icon in a diminishing way as the oxygen is used over time.

In an example, the Injection Icon 224 is modified after administration of a medication such that the icon shows a badge, this badge indicating the number of times a medication has been administered.

In an example, when the Operator long-presses an icon, such as the Injection Icon 224, additional details related to that icon's function are presented in the display, such as the time elapsed since the administration of a medication. In an example, when the Operator double-taps an icon or right-clicks an icon or force-clicks an icon, a menu appears providing the Operator additional functions related to that icon, such as enabling detailed information to the Log, or sending a message related to the icon.

When the Operator has dropped the selected Action Icon 220, the application prompts the Operator to select the specific medication or delivery protocol.

In an example, the Operator double-clicks on an Action Icon 220, the software then changing the state of the Action Icon, The Operator then clicks on the Patient Icon 210, the software then changing the state of one or both of the Patient Icon and the Action Icon to reflect the use of the action.

Medication or Service Delivery

In an example, after dropping an Action Icon 220, a new icon such as the Medication Icon 230, appears on the interface to prompt the Operator, where previously this icon had been hidden from view.

In an example. after dropping an Action Icon 220, an associated icon which has already been shown on the interface, such as the Medication Icon 230, changes its color to prompt the Operator.

In an example, when the Operator selects a desktop icon representing delivery of medication, the Medication Icon 230, the application presents a Medication Drop-down 232 to the Operator representing specific medications such that the Operator may select one or more of the medications as a detail in the event at hand. After the Operator has selected the medication from the drop-down, the drop-down disappears from the interface and reverts to showing only the Medication Icon 230.

It may be understood, by similar explanation, that selection of an Equipment Icon 220 or Service Icon 270, for which details other than medication selection are needed, includes prompting with icons for the details on the use of the selected equipment or service.

In an example, if an incision is required, a scalpel icon is selected by the Operator and placed on the Patient Icon. The application prompts the Operator with a drop-down menu for the exact location of the incision.

Personnel

In an example, when the Operator selects a desktop icon representing delivery of medication, and after the Operator has selected the medication from the Medication Drop-down 232, the application presents a Personnel Drop-down 242 to the Operator representing each of the personnel present at the event such that the Operator may select the person performing the action with the medication. After the Operator has selected the person or role from the drop-down, the drop-down disappears from the interface and reverts to showing only the Personnel Icon 240.

In an example, the Personnel Drop-down 242 is constructed by recognizing personnel as they enter or leave the scene of the event and updating the drop-down list accordingly during the course of the event.

In an example, the recognized personnel are listed in the user interface according to their role in the medical situation, and not including the names of personnel, the role, such as doctor, registered nurse, physician assistant, respiratory therapist, nurse practitioner, emergency medical technician (EMT), paramedic, being the information most useful to the user when selecting a person performing an action.

In an example, the records of the medical incident are supplemented after the event by inserting into the event data the name of each person recognized by role.

In an example, the Personnel Dropdown 242 is modified to show only those personnel who have a customary scope of professional practice consistent with the previously-selected action.

In an example, when some attending personnel have previously been selected to show their involvement in ongoing actions, the application marks these personnel in a distinctive manner to indicate to the Operator that these personnel are not likely candidates to assign to the new action, even if they are qualified to perform the new action. The distinctiveness may be by showing different color or shading.

Parallel Medical Actions

In an example, the Recording User Interface 200 allows the Operator 150 to initiate the recording of a second Medical Action before completing the recording of the current Medical Action. If Medical Actions are taking place during the CPR Event more quickly than the Operator can complete recording of each event in turn, then the application allows the Operator to select icons to start a second or subsequent recording while icons or drop-downs or other elements are still open on the user interface for the first event.

In an example, the application changes the appearance of user interface elements associated with a pending Medical Action while the Operator begins recording of a second Medical Action, such that the interface elements for one event are not confused with interface elements for the second event.

In an example, as the Operator completes recording of the details for one Medical Action, the application reverts the appearance of previously altered interface elements to their original state, and provides feedback to the Operator to return to the interface elements for previous Medical Actions to complete the recording of those events' details.

In an example, the application notifies the Operator 150 through the use of audio cues from Audio Generator 280 or other means, or visual cues, or both, when the Operator has made an invalid selection or omitted required information or has made a valid selection, each notification with unique indication.

Figure 5:
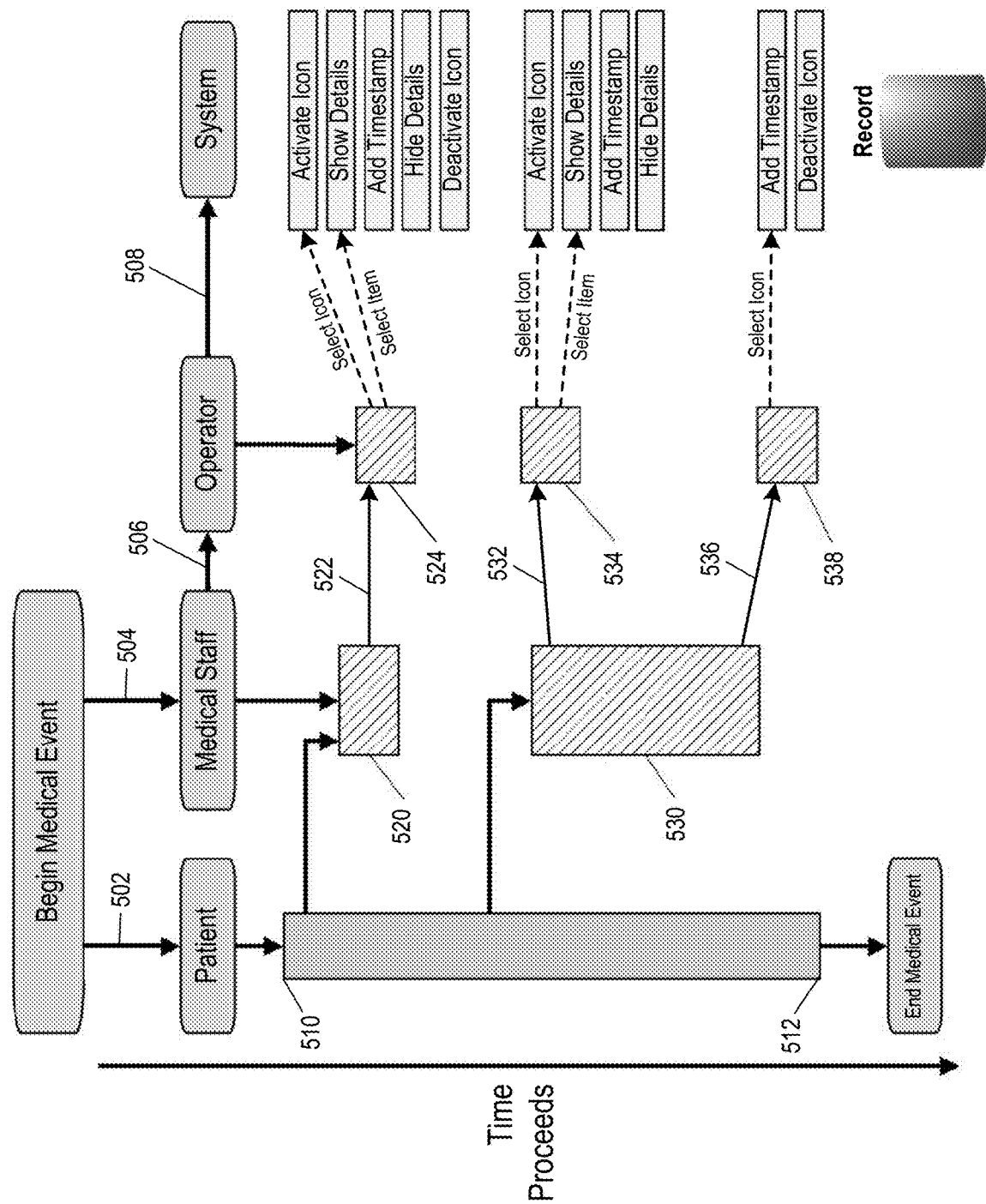
FIG. 5 is a flow diagram of a process in which an operator may record the actions performed during the emergency event by interacting with a plurality of icons.

The Operator 150 interactions with the Recording User Interface 200 to handle multiple Medical Actions is shown in FIG. 5 as an example. The CPR Event begins with the Patient Entering the CPR Event Space 502 and the Medical Staff Entering the CPR Event Space 504. The Operator prepares to observe 506. The Operator readies the System to record 508. The CPR Event has an Event Start 510 and an Event End 512. The Medical Staff performs a Brief Medical Action 520. This action is observed 522 by the Operator, who then selects or drags-and-drops an icon 524 in the System. The System puts the selected icon through several states, such as when the Operator selects items from the icon's details. The Brief Medical Action concludes and the Operator finishes using the selected icon. The System records the time, closes the details, and deactivates the icon. Examples of a Brief Medical Action are affixing an oxygen mask to the Patient, and injecting a medication into the Patient.

FIG. 5 continues and shows an Ongoing Medical Action 530. An example of an Ongoing Medical Action is applying chest compressions. The beginning of the action is observed by the Operator 532, who then selects an icon 534, and provides details as prompted. Note that the System maintains the selected icon in the active state until the Operator observes the conclusion of the action 536 and deselects the icon 538. At that point, the System records the time and other data in the Record and deactivates the icon.

Figure 8:
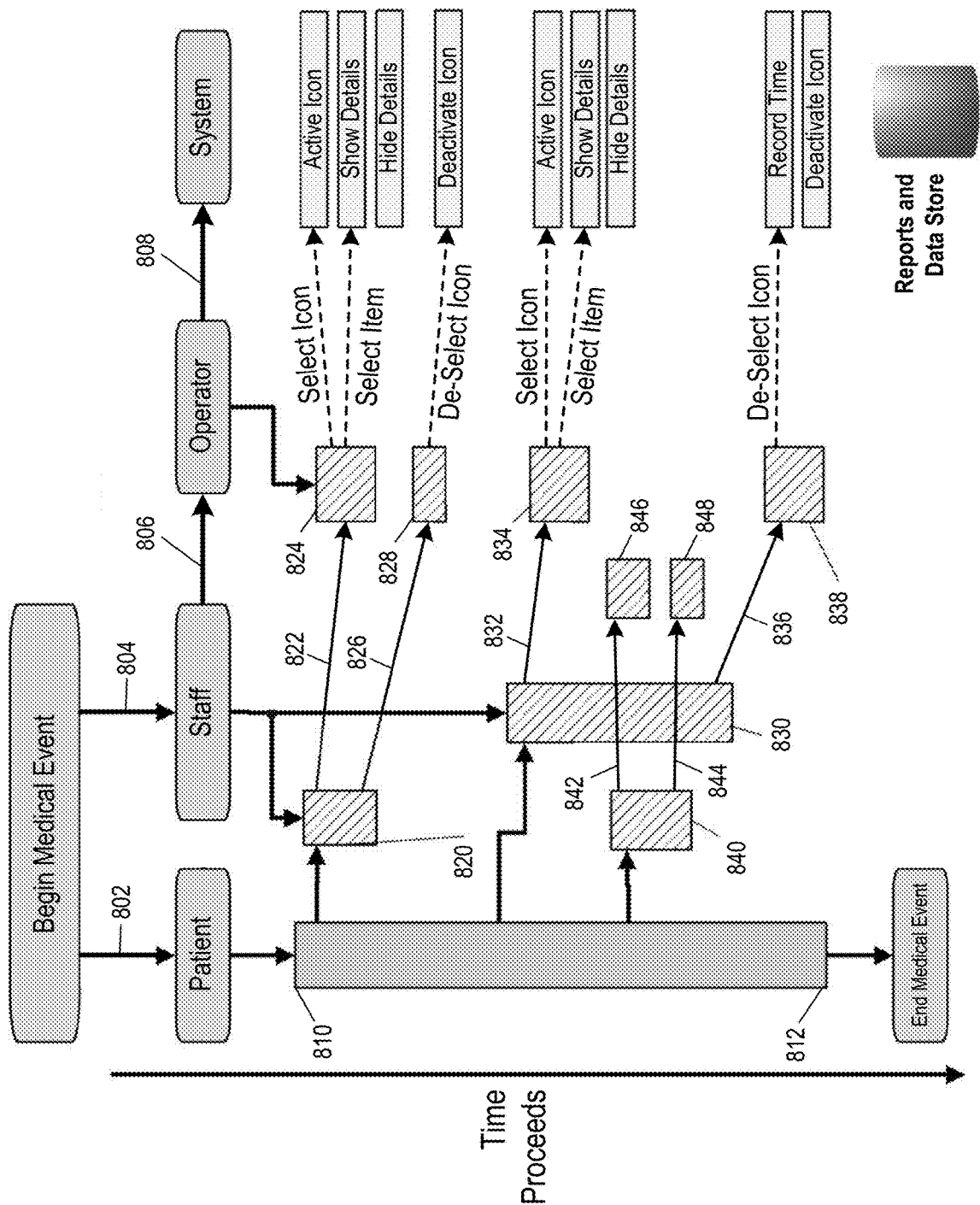
FIG. 8 is a flow diagram of a process in which an operator is able to handle multiple coincident medical actions using icons.

Additional Medical Actions may occur during the time when an existing Ongoing Medical Action 530 is in process. This more complex sequence is shown in FIG. 8 as an example. The CPR Event begins with the actions of "the Patient Entering the CPR Event Space" 802 and "the Medical Staff Entering the CPR Event Space" 804. The Operator prepares to observe 806. The Operator readies the System to record 808. The CPR Event has an Event Start 810 and an Event End 812. The Medical Staff performs an Ongoing Medical Action 820. This start of the action is observed 822 by the Operator, who then selects or drags-and-drops an icon 824 in the System. The System puts the selected icon through several states, such as when the Operator selects items from the icon's details. The Ongoing Medical Action concludes 826 and the Operator finishes using the selected icon 828. The System records the time, closes the details, and deactivates the icon.

FIG. 8 continues and shows a second Medical Action 830, beginning after the completion of the first Medical Action 820 yet not completing before a third Medical Action 840 also begins. The Operator observes, in turn and in real-time, the beginning of each Medical Action, 822 and 832 and 842.

The Operator selects the appropriate icon for each Medical Action, 824 and 834 and 844, and provides necessary details. The System activates each icon when selected by the Operator and maintains the state of each icon separately. (The states of the icon for Medical Action 830 are not shown for clarity in the figure.) The System concludes each icon as the Operator performs the selections.

In an example, faults and reminders to the Operator are logged into the Log 260 with time stamps to indicate when such application events took place.

In an example, The Recording System may simulate one or more of the Medical Events with the actions of a fictitious Patient acting out a CPR Event for the purpose of training the Operator 150, It may be understood, by similar means, that when the Operator selects an Equipment Icon such as the Oxygen Icon 222 or the Defibrillator Icon 246 the corresponding detail icons and/or drop-downs appear on the interface. It may be understood, by similar means, that the Operator may be presented with different icons, each representing a different means of oxygen administration, such as blow by, nasal cannula, bag valve mask (BVM), nasal prongs, nasal trumpet, and oral airway.

Administration

In an example, the Operator 150 is provided with means to change the set of Icons 240 at the Desktop 230 level, and/or at other levels within the application.

In an example, the Icons 240 may be changed only by an administrator, and not by the individual Operator 150, to maintain consistency across multiple Recording Devices 110.

In an example, the Icons 240 may be configured based on information received by or entered into the Recording Device 110. For example, when the Patient's name and medical allergies are available to the Recording Device, then the Medication Icons 246 are limited to only those medications compatible with the Patient.

In an example, the set of Personnel Icons 244 in the Recording Device is updated when the set of personnel in the CPR Event Space 160 changes in real time, such that the Operator selects from Personnel Icons 244 for only those people present.

In an example, the real time updating of Personnel Icons 244 in the CPR Event Space 160 is performed by communication from the CPR Event Space ID badge entry system to the Recording Device 110. Examples of CPR Event Space ID badges may be RFID badges, swipe badges, photo ID badges, each work by personnel in the CPR Event Space.

In an example, when the number of items of a particular type of equipment is consumed during the CPR event, the Equipment Icon 220 representing that type of equipment is automatically removed from the user interface, and only reappears when the equipment is resupplied.

In an example, the real time updating of Equipment Icons 220 in the CPR Event Space 160 is performed when the Recording Device 110 moves from one location to another, such as from one operating room to another operating room, using the Location System 146 in the Recording Device.

A key aspect of the implemented user interface is keeping the Operator's 150 fingers or pointing devices on the Recording Device 110, inputting medical actions and details of actions with minimal textual input. The use of icons reduces the number of finger or pointer device actions by the Operator, thereby assisting the Operator in keeping pace with the flow of Medical Actions during the CPR event.

A second aspect of the user interface is the limiting of options presented to the Operator 150 at each stage of selecting a medical action or entering medical action details. For example, when selecting a specific Equipment Icon 242, the Operator is presented with details related only to that specific equipment. When selecting a specific Medication Icon 244, the Operator is presented with details such as dosage, form, concentration or route of administration, related only to that specific medication.

In an example, the Recording Device 110 is a laptop computer.

In an example, the Recording Device 110 is a smart tablet or smart phone.

In an example, the Recording Device 110 is a desk-mounted computer.

In an example, the Recording Device 110 is a specially-designed computer.

In an example, the Recording Microphone 130 may be integrated into the Recording Device 110.

In an example, the Recording Microphone 130 may comprise one or more microphones, each mounted in a position within the CPR Event Space 160 to accurately capture the voice of the Operator 150.

In an example, the Camera 140 may be integrated into the Recording Device 110.

In an example, the Camera 140 may comprise one or more cameras, each mounted in a position within the CPR Event Space 160 to accurately capture the gestures of the Operator 150, the Recording System 100 selecting one or more of the cameras for a view of the Operator as the Operator and other personnel may move through the CPR Event Space.

In an example, the one or more Speakers 134 may be integrated into the Recording Device 110.

In an example, the one or more Speakers may be supplemented by, or replaced by the Headset 132, worn by the Operator 150.

In an example, the Keyboard 144 may be a virtual keyboard displayed on the Touch Screen 114.

In an example, the Location System 146 may be based on one or both of GPS and network signals.

Recording User Interface

The Recording User Interface 200 may present selected information and prompts to the Operator 150 according to one or more of Operator actions, these actions including one or more of single- and multi-finger touches, taps and swipes and the like. The Recording System 100 prompts the Operator for input at one or more steps, each step corresponding to the Operator's selection of an action from among the actions possible during a CPR event.

The Recording User Interface 200 may use colors and standardized icons to facilitate prompt recognition of choices and actions by the Operator 150 during the CPR event.

In an example, the Recording System 100 may use the Audio Generator 280 to create tones or audible cues as part of the system of guiding the Operator from step to step in the recording process.

In an example, the Icons 240 presented to the Operator 150 may be adjusted on the Display Screen 112 to reflect changes in one or more of the equipment, personnel, medications available at the time during the course of the CPR event. Icons representing a collection of more than one of a type of equipment or personnel or medication may be superimposed on the Display Screen to save space on the screen. For example, multiple scalpels may be shown as a series of overlapping icons, each for one scalpel; or as a single icon with an indication of the number of scalpel available at that time.

In an example, Icons 240 may move on the Display Screen 112 to represent their changing positions in the CPR Event Space 160, this adjustment of icon position facilitating the Operator's 150 selection of a resource using its icon placed similar to the Operator's point of view in the space.

In an example, Icons 240 may remain in fixed locations on the Display Screen 112 to provide unchanging icon arrangement to facilitate Operator's 150 selection of the appropriate icon.

In an example, the Operator 150 may input information or makes selections using one or more of the Touch Screen 114, the Recording Stylus 120, the Recording Microphone 130, the Touchpad 132, and the Keyboard 144.

In an example, the Operator 150 may input information through gestures, recognized by the Camera 140.

In an example, the Operator 150 may wear a Headset 132 which includes an augmented reality (AR) device. The Operator views the CPR Event Space 160 though the AR device. The virtual user interface is within the view of the AR device worn by the Operator and implements one or more of the functions of the Recording User Interface 200. The Operator selects the image of one or more object in the view of the AR device. The Operator may input information or make selections using gestures or a virtual pointing device. The gestures and/or virtual pointing device act on virtual representations of input devices. Virtual input devices include one or more of a virtual touch screen, a virtual touchpad, a virtual keyboard, a virtual tablet, and a virtual smart phone. Through the use of the AR device and the virtual user interface, the Operator may perform one or more of the functions otherwise performed using the physical Recording User Interface and physical input devices.

In an example, the Operator 150 may input information and/or make selections using a combination of the physical Recording User Interface 200 and physical input devices, and the virtual user interface and virtual devices.

In an example, features of the Recording User Interface 200 may include processing of audio input from the Operator 150 such as voice or auditory indications. The processing may result in the input of information and/or making selections.

In an example, the Recording System 100 may store the recorded audio input from the Operator 150 and/or the medical professionals during the Medical Event as a record for later analysis. For example, the recorded audio input may be stored in a memory that is internal to the Recording System 100, or the recorded audio input may be stored in a memory that is accessible to the Recording System (e.g., via a network).

In an example, features of the Recording User Interface 200 include aspects of occlusive virtual reality user interfaces, creating an overall simulated reality experience for the Operator 150 in the CPR Event Space 160.

In an example, recorded data is passed directly among interconnected devices in the CPR Event Space and middleware is used to normalize the data format such that a sequence of data records is recorded by the recording device without the interaction by the operator, these data records containing time stamped details on events and processes during the CPR Event.

Recording System Flowchart

The Operator 150 observes the activities and communications in the CPR Event Space 160. At each action during the CPR event, the Operator selects one or more of the representations on the Display Screen 112, corresponding to the type of action which has occurred. For example, the Doctor calls out that the Patient has experienced respiratory failure. The Doctor calls for an intubation using an anesthesia intubation blade. The Operator selects this piece of equipment using its icon. The Recording User Interface 200 opens a Prompt Window 250, with details listed appropriate to that piece of equipment, such as blade size and endotracheal tube size. The Doctor calls out the required blade size and endotracheal tube size, whereupon the Operator selects those details from the Prompt Window. When the required details have been selected or entered or defaulted to previously-set values, the Operator closes the Prompt Window, or the Prompt Window closes automatically. A time stamp is applied to the action defined by the selected Prompt Window and the details therein. This time stamp is a measure of time along the time line of the CPR event, the time measured to the level of seconds. At the conclusion of recording for each action, the Operator is presented with a Confirmation Window 260.

Concurrent with the entry of action details in a Prompt Window 250, the Operator 150 may select one or more Sub-Windows 252 in which to record the result of the action taken, the result being associated with the action by the association of Sub-Window to Window, with no additional action required of the Operator to denote such association. For example, after intubation with an endotracheal tube, the Operator records the flow rate and respirator rate of the Patient. A time stamp is attached to the information in the Sub-Window.

More than one Prompt Window 250 may be opened at the same time on the Display Screen 112 when there are medical actions to be recorded which are occurring in parallel in the CPR Event Space 160. For example, the Doctor may call out an medical action, immediately followed by a separate event from the Doctor before the first medical action has been completed.

In an example, Icons 240 for equipment or medication may be dragged onto an Icon for the Patient and dropped there, denoting that the equipment has been in use with the Patient, or that the medication has been given to the Patient. In each such medical action, the details of the action are recorded using Prompt Windows 250 opened as a result of the drag-and-drop operation.

System Status Indicators 290 may at any time during the CPR event indicate a change in system condition which affects the ability of the Operator 150 to record medical actions, or the ability of the Recording System 200 to record medical actions, or both. Such indications by System Status Indicators are brought to the Operator's immediate attention.

The Audio Generator 280 is used to create notifications for system status changes, for invalid entries into Prompt Window 250, and for medical action initiation.

In an example, the Audio Generator 280 is used to highlight critical events, such as cardiac arrest.

In an example, one or both of Menu Bars 250 and Tool Bars 220 are used to select operations outside of the CPR event, such as system configuration, system update and export of reports. In order to optimize the efficiency of the Operator during the CPR Event, Menu Bars and Tool Bars are not used to record medical actions. Such Menu Bars and Tool Bars may be hidden from view on the Desktop 230 during the CPR Event.

Figure 6:
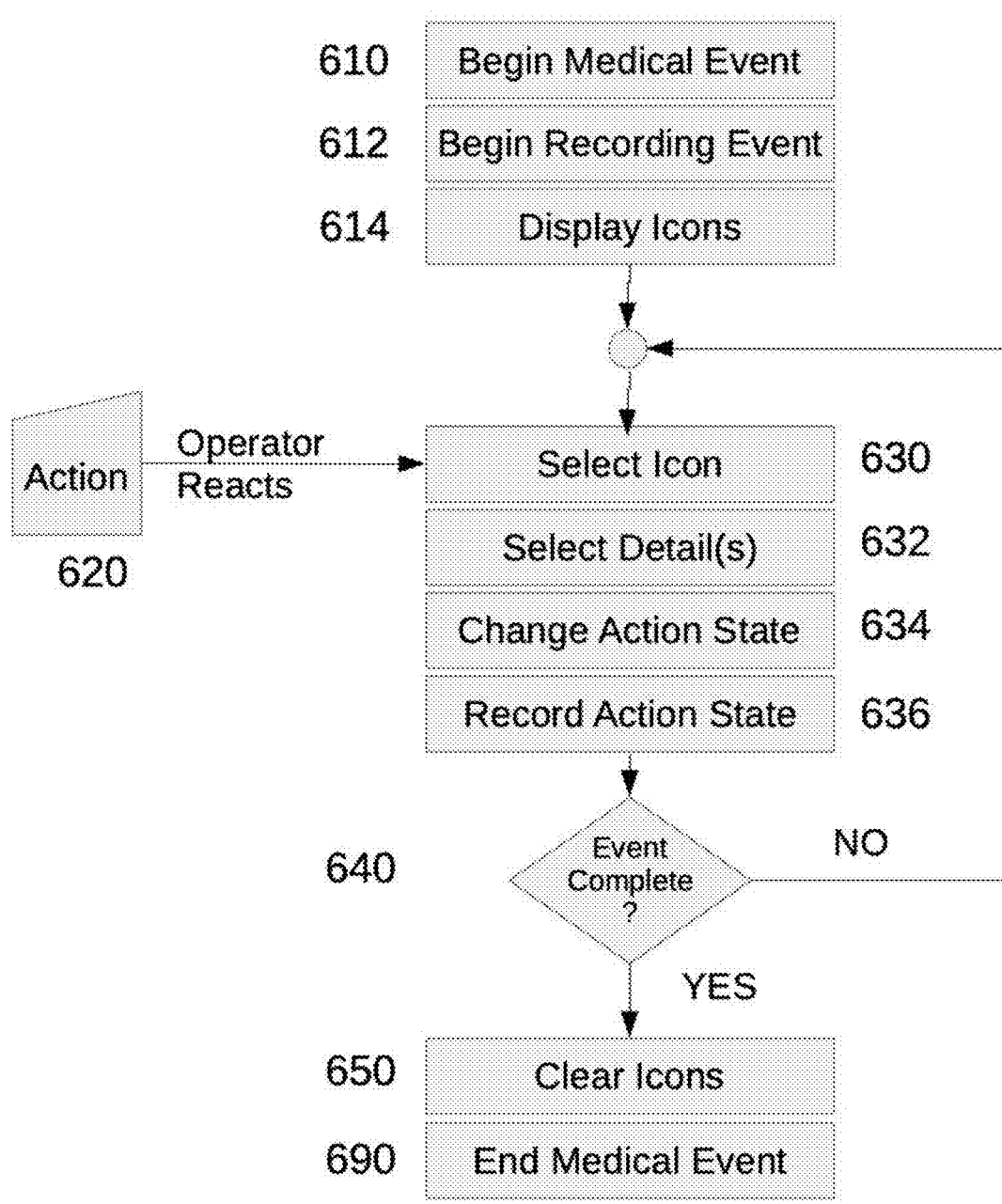
FIG. 6 is a sequence diagram of a process of interacting with the operator through icons.

FIG. 6 shows the CPR Event Beginning 610, when the System begins recording the CPR Event 612 and the System displays a suite of icons 614 for the Operator. As each Medical Action 620 occurs, the Operator selects an icon 630 and selects relevant details 632. The System maintains the state of the selected icon 634 and records the time and selected details 636. This sequence is repeated for each Medical Action until the Event is completed 640. When completed, the System clears the icon states and makes the icons inaccessible to the Operator 650. The CPR Event ends 690 when all actions have been entered and recorded. The conventional system of recording medical actions during a CPR event involves the use of one or more Forms 310, each Form organized as a set of Entry Fields 320.

In some examples, the Form 310 is organized as a tabular series of Entry Fields 320, each in the series to be used for recording one medical action; the sequence of recorded medical actions to match the sequence of medical actions in the CPR Event Space 160.

In some examples, each medical action during the course of the CPR event is recorded on a separate Form 310; the series of Forms compiling a sheaf of detailed records of the medical actions.

The Operator 150 uses the Forms 310 to record details for each medical action, putting data into the Entry Fields 320 on each Form, using the names of equipment, personnel, medications and similar details. The Operator may be expected to include a time stamp for each medical action by referring to a timekeeping device in the CPR Event Space 160. If the Operator falls behind the real-time sequence of medical actions, unable to record all necessary detail before the next medical action occurs, then the details may be entered after the fact. The Forms do not prompt the Operator to complete or confirm the data entry before moving on to the next Form.

This process of call, record and confirm is repeated through the course of the CPR event, with the Operator recording medical actions coming from Personnel as they occur. The Operator is shown only those options relevant to the equipment, such as ECG, or medication. The personnel associated with each event is only selected from a set representing the personnel in the CPR Event Space 160 at that point in time. The specification of equipment details or medication details as entered by the Operator are checked automatically by the Recording System 200.

Each action during the CPR event is recorded by the Recording System 200, the Recording System creating one or more files, databases or computer records. The data is formatted in a consistent and regularized manner, such as using, but not being limited to, the framework and ontology of the Standardized Nomenclature for Medicine—Clinical Terms (SNOMED-CT). This regularization provides a data store which is compatible, or can be made compatible, with a variety of software systems and tools, all using a definite meaning attached to each term.

The collection of recorded actions becomes part of the medical record of the Patient, such as HIPAA-compliant electronic medical records (EMR) or electronic health record (EHR), to facilitate analysis of operations and patient care.

Analysis System

Analysis of the recorded details of actual medical events provides an assessment of the actions taken by the medical professionals in the real work environment, comparing those actions to the prescribed actions in the one or more professional standards. Patterns of adherence are listed by the analysis, as well as patterns of non-adherence or fault. The assessment evaluates the performance of each individual across multiple medical situations, as well as evaluating the performance of teams, composed of combinations of individuals, across multiple medical situations.

In an example, analysis of the recorded details of simulated medical events provides an assessment of the actions taken by medical professionals in a simulated situation.

In an example, the analysis of the recorded details is performed by machine learning and/or artificial intelligence software, these methods providing effective analysis of large, aggregated databases of medical event details, in particular an analysis of variations in the performance of actions during the Medical Event.

In an example, aggregated data may span one or more of a timeline of Medical Events at one facility, a timeline of events across multiple facilities, and a timeline of events across multiple teams of medical professionals.

In an example, metadata on each Patient is collected and attached to the data recorded for each Medical Event, such that the analysis of the aggregated data may be across various comorbidities.

Figure 7:
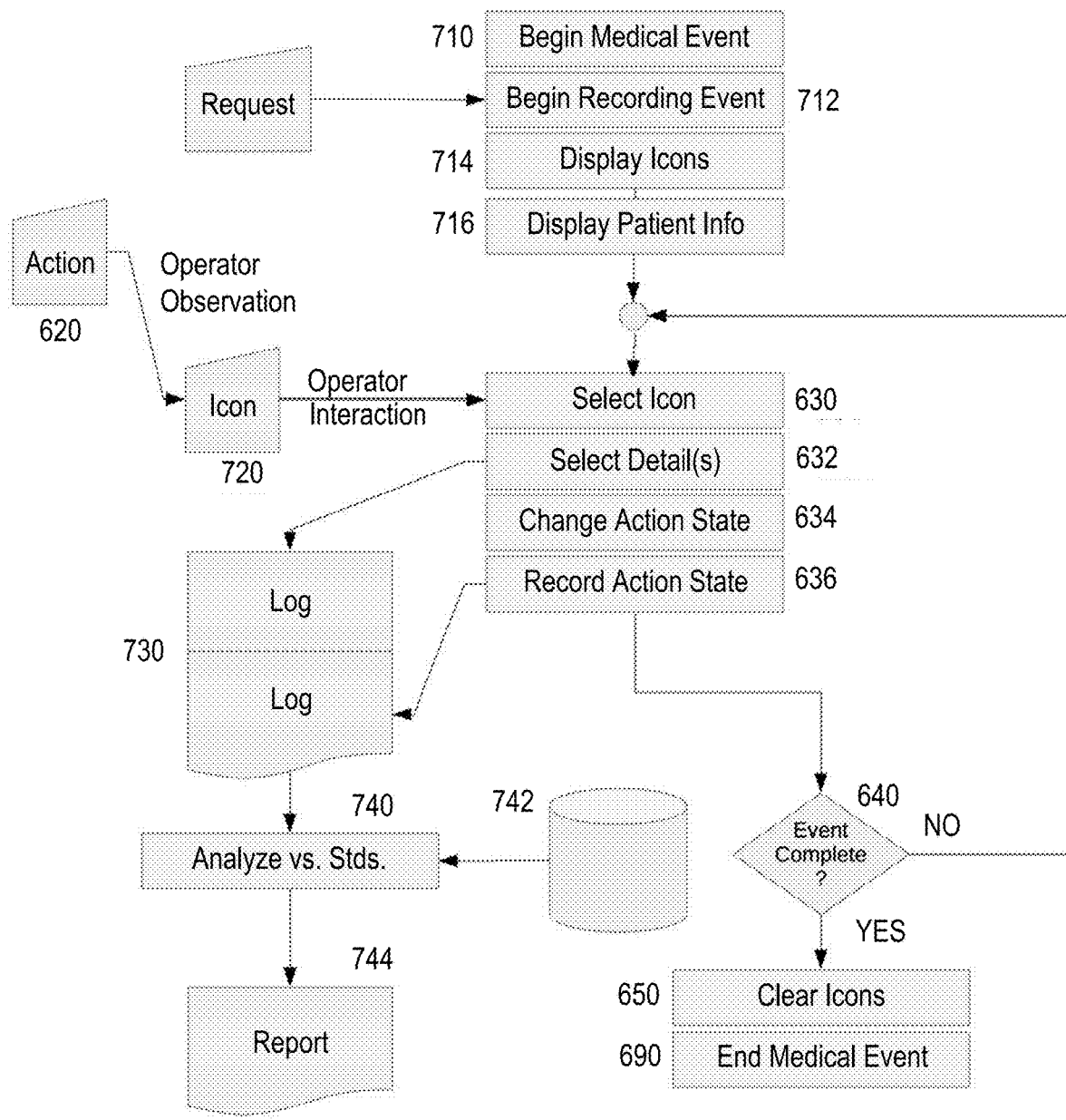
FIG. 7 is a flowchart of a process for handling the operator's instructions through interactions with icons, and logging the actions.

FIG. 7 shows the beginning of the CPR Event 710, the Begin Recording 712, the setup of icons 714, and the Patient Information Display 716. Each Medical Action 620 causes the Operator to select an Icon 720. The System manages the icons' states as described for FIG. 6, and records information in one or more Log 730. The Logs are Analyzed 740 against Standards Definitions 742 to produce one or more Reports 744.

Analysis of the recorded details of actual medical events also correlates the event details to the actions taken and the immediate clinical outcome of each event, including statistics such as mortality; morbidity; in the context of CPR events, results of: surgical procedures, medication administration, compressions, fluid administration, cardioversion, defibrillation, and other procedures. Strengths in the professionally-prescribed protocols are determined by statistically positive medical outcomes, when nulling out the variation due to individual medical professional's performance to the standards. Weaknesses in the professionally-prescribed protocols are determined in similar manner.

This analysis is particularly powerful in affecting future patients since many of the professionally-dictated protocols describe life-or-death medical life support situations, these protocols being updated on a regular basis using what has been learned from outcomes, scientific literature, and analysis of events.

The strengths and weaknesses identified in the standard protocols provide insights which lead to modifications of those protocols in areas of weakness, adoption of protocols by other, similar standards in areas of strengths, and clarification of protocol details in areas of ambiguity.

The in-depth analysis of performance and the protocols is not practical when attempted manually by viewing and reviewing the recorded information: because the professional protocols continue to evolve on a schedule which requires input for modifications in a timely manner; and because evaluation of professionals' individual and team performance is required on a short, repeating schedule, such as four times per year; as well as when various related standards are updated, such as annually.

The system of recording and analysis provides explicit, quantitative, statistical information. This information is more useful, more accurate than the implicit analysis performed manually in current organizations by those supervising medical professionals. The improved information is actionable.

The outcomes of the analysis may be traced back to the specific recorded situations, thereby providing a closed-loop system for reinforcing adherence to protocols and rectifying non-adherences or faults.

The system of recording and analysis allows the improved information to be aggregated across multiple medical organizations. Assessments of the professionally-prescribed protocols may be combined to reinforce strength and weakness evaluations, and to find factors which explain the variations in protocol adherence. These factors may not be evident when analyzing the data from one medical institution, such as variation due to seasonal changes, demographic differences in the patient population, demographic differences in the professionals' population, differences in management structure across multiple organizations.

The aggregated analysis is fed back to the professional organizations which are responsible for the professionally-dictated protocols. Those groups may then make modifications to the protocols based on real world data, including the accuracy of data.

In addition to affecting individuals, teams, organizations and standard-setting bodies, the outcomes from the system of recording and analysis may be used to publish in journals, books and other formats, both juried and non-juried, such as informing the public of improvements in life support protocols, or ranking performance to existing protocols across multiple institutions.

The system of recording and analysis provides information which leads to changes in human behavior, including improvements in medical performance, improvements in consistent care, improvements in medical outcomes, and improvements in training as modified protocol standards are used in subsequent training cycles.

In the description above, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form. There may be intermediate structure between illustrated components. The components described or illustrated herein may have additional inputs or outputs that are not illustrated or described. The illustrated elements or components may also be arranged in different arrangements or orders.

Many of the apparatuses are described in their most basic form. It will be apparent to those skilled in the art that many further modifications and adaptations may be made. The particular embodiments are not provided to limit the invention but to illustrate it.

If it is said that an element "A" is coupled to or with element "B", element A may be directly coupled to element B or be indirectly coupled through, for example, element C. When the specification states that a component, feature or structure A "causes" a component, feature or structure B, it means that "A" is at least a partial cause of "B" but that there may also be at least one other component, feature or structure that assists in causing "B". If the specification indicates that a component, feature or structure "may", "might", or "could" be included, that particular component, feature or structure is not required to be included. If the specification refers to "a" or "an" element, this does not mean that there is only one of the described elements.

Overview of Recording System

Figure 9:
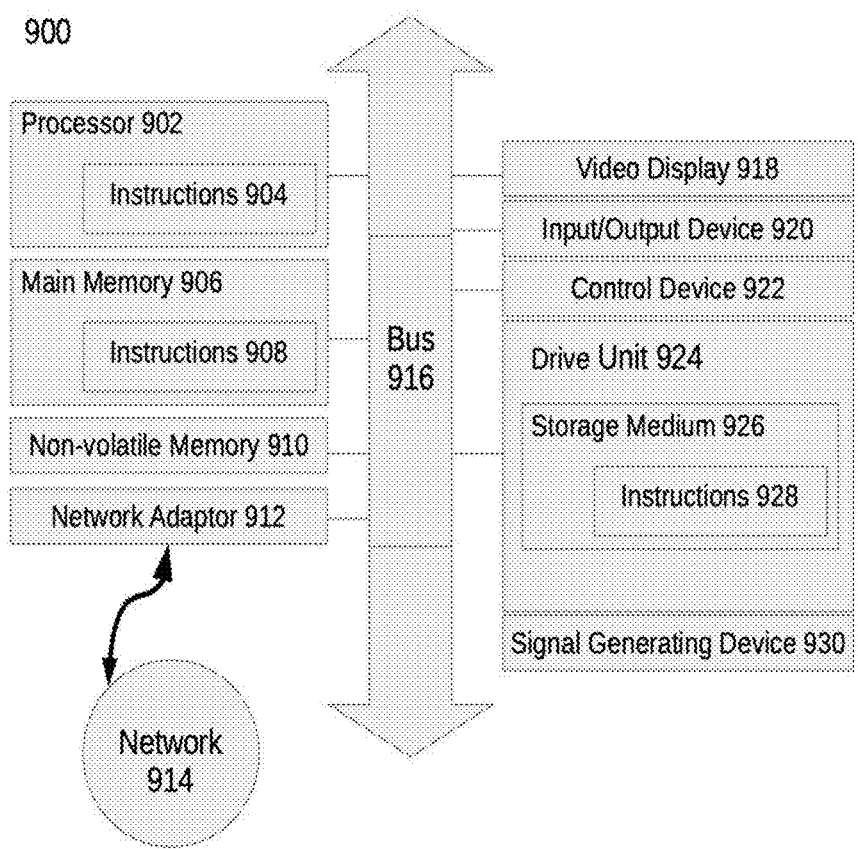
FIG. 9 is a block diagram illustrating an example of a processing system in which at least some operations described herein can be implemented.

FIG. 9 is a block diagram illustrating an example of a processing system 900 in which at least some operations described herein can be implemented. For example, components of the processing system 900 may be hosted on a computing device that generates the user interfaces shown in FIGS. 2A-E. Said another way, components of the processing system 900 may be included in a recording device (e.g., Recording Device 110 of FIG. 1).

The processing system 900 may include a processor 902, main memory 906, non-volatile memory 910, network adapter 912 (e.g., a network interface), video display 918, input/output device 920, control device 922 (e.g., a keyboard, pointing device, or mechanical input such as a button), drive unit 924 that includes a storage medium 926, or signal generation device 930 that are communicatively connected to a bus 916. The bus 916 is illustrated as an abstraction that represents one or more physical buses and/or point-to-point connections that are connected by appropriate bridges, adapters, or controllers. The bus 916, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit (I2C) bus, or bus compliant with Institute of Electrical and Electronics Engineers (IEEE) Standard 1394.

The processing system 900 may share a similar computer processor architecture as that of a computer server, router, desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify action(s) to be taken by the processing system 900.

While the main memory 906, non-volatile memory 910, and storage medium 924 are shown to be a single medium, the terms "storage medium" and "machine-readable medium" should be taken to include a single medium or multiple media that stores one or more sets of instructions 926. The terms "storage medium" and "machine-readable medium" should also be taken to include any medium that is capable of storing, encoding, or carrying a set of instructions for execution by the processing system 900.

In general, the routines executed to implement the embodiments of the present disclosure may be implemented as part of an operating system or a specific application, component, program, object, module, or sequence of instructions (collectively referred to as "computer programs"). The computer programs typically comprise one or more instructions (e.g., instructions 904, 908, 928) set at various times in various memories and storage devices in a computing device. When read and executed by the processor 902, the instructions cause the processing system 900 to perform operations to execute various aspects of the present disclosure.

While embodiments have been described in the context of fully functioning computing devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile and non-volatile memory devices 910, removable disks, hard disk drives, optical disks (e.g., Compact Disk Read-Only Memory (CD-ROMS) and Digital Versatile Disks (DVDs)), cloud-based storage, and transmission-type media such as digital and analog communication links.

The network adapter 912 enables the processing system 900 to mediate data in a network 914 with an entity that is external to the processing system 900 through any communication protocol supported by the processing system 900 and the external entity. The network adapter 912 can include a network adaptor card, a wireless network interface card, a switch, a protocol converter, a gateway, a bridge, a hub, a receiver, a repeater, or a transceiver that includes an integrated circuit (e.g., enabling communication over Bluetooth or Wi-Fi).

The techniques introduced here can be implemented using software, firmware, hardware, or a combination of such forms. For example, aspects of the present disclosure may be implemented using special-purpose hardwired (i.e., non-programmable) circuitry in the form of application-specific integrated circuits (ASICs), programmable logic devices (PLDs), field-programmable gate arrays (FPGAs), and the like.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

While embodiments may be described in the context of generating a single log, those skilled in the art will recognize that the process may be similarly applicable if multiple logs (e.g., for different cardiac events, different patients, etc.) are generated. Thus, the processor may generate one or more logs.

While embodiments may be described in the context of single- or double-click using a mouse, those skilled in the art will recognize that the process may be similarly applicable if the action or actions include triple-click, clicks of various distinguishable pressures, taps, and the like, executed with a pointing device such as stylus.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the preceding claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A non-transitory medium with instructions stored thereon that, when executed by a processor of a recording device, cause the recording device to perform operations comprising:
   receiving input indicative of a request from an operator to initiate recording of actions performed during an emergency medical event that takes place in an emergency event space that is under observation by the recording device or another computing device that is communicatively connected to the recording device;
   causing display of an interface that includes (i) a representation of a patient, (ii) a first plurality of icons that are representative of medications available in the emergency event space, and (iii) a second plurality of icons that are representative of personnel,
      wherein the personnel in the emergency event space are identified based on an analysis of (i) images of the emergency event space or (ii) records of physical badges being used to access the emergency event space; and
   over the course of the emergency medical event,
      receiving, via the interface, inputs that are indicative of drag-and-drop engagements with the first and second pluralities of icons,
         wherein each drag-and-drop engagement corresponds to a real-world action performed during the emergency medical event, as recorded by the operator by dragging an appropriate one of the first and second pluralities of icons onto the representation of the patient;
      recording, in a data structure, actions performed in real time through continuous recognition of the drag-and-drop engagements,
         wherein each drag-and-drop engagement is represented, in the data structure, with (i) an indication of the real-world action and (ii) a time stamp that indicates when the operator completed that drag-and-drop engagement and when the real-world action was performed;
      adjusting visual appearances of the first plurality of icons based on the drag-and-drop engagements, such that each one of the first plurality of icons that is involved in one of the drag-and-drop engagements is accompanied by a digital badge indicating a number of times that a corresponding one of the medications was administered; and
      adjusting the first and second pluralities of icons presented on the interface based on an analysis of data generated by either the recording device or the other computing device, so as to reflect changes in the medications available in the emergency event space and the personnel present in the emergency event space.

2. The non-transitory medium of claim 1, wherein the operations further comprise:
   receiving another input indicative of a selection of a given icon from amongst the first and second pluralities of icons;
   initiating an action that corresponds to the given icon; and
   modifying the given icon to indicate a state of the action.

3. The non-transitory medium of claim 2, wherein said modifying comprises:
   altering the given icon to include a textual label that indicates the state,
   adjusting a transparent of the given icon to indicate the state, or
   adjusting a color setting of the given icon to indicate the state.

4. The non-transitory medium of claim 1, wherein the interface further includes:
   at least one equipment icon that permits the operator to indicate use of a piece of equipment during the emergency medical event.

5. The non-transitory medium of claim 1, wherein the operations further comprise:
   generating, based on the drag-and-drop engagements with the first and second pluralities of icons, a log of the actions that serves as a non-transient record of the emergency medical event.

6. A method comprising:
   receiving, by a processor, input indicative of a request to initiate recording of an emergency medical event in which treatment is provided to a patient in an emergency medical space;
   causing, by the processor, display of an interface that includes icons corresponding to different items available in the emergency medical space;
   receiving, by the processor, a series of inputs indicative of drag-and-drop engagements with the icons over the course of the emergency medical event,
      wherein each input corresponds to a drag-and-drop engagement, by an operator, with a corresponding icon that serves as an indication that an action involving a corresponding item was performed with respect to the patient;
   adjusting, by the processor, visual appearances of the icons based on the series of inputs provided by the operator, such that each one of the icons that is involved in one of the drag-and-drop engagements is accompanied by a digital badge indicating a number of times that the corresponding item was used; and
   recording, by the processor, the emergency medical event by—
      generating a log with entries corresponding to the drag-and-drop engagements arranged in temporal order,
         wherein the log serves as a non-transient record of actions performed over the course of the emergency medical event, and
         wherein each entry includes (i) an indication of a corresponding one of the actions and (ii) a time stamp that indicates when the operator completed that drag-and-drop engagement and when the corresponding action was performed, and
      storing the log in a memory.

7. The method of claim 6, wherein the processor records an action responsive to a determination that a given icon was dragged and then dropped proximate to a digital representation of the patient.

8. The method of claim 6, wherein the icons are presented as a set according to the items available in real time in the medical event space in which the emergency medical event is managed.

9. The method of claim 6, wherein the memory is accessible to the processor across a network.

10. The method of claim 6, further comprising:
receiving, by the processor, input indicative of a secondary interaction with a particular icon;
reacting, by the processor, to a change in state of one or more items represented by icons, with the state change determined by the input interaction by the operator; and
causing, by the processor, display of a digital element that permits the operator to provide additional information regarding a given action.

11. The method of claim 10, wherein the digital element is a drop-down list that provides multiple options for performing the given action.

12. The method of claim 6, wherein the interface is accessible via a mobile application executing on a mobile device.

13. The method of claim 6, wherein the time stamps are at the level of seconds for each action, as recorded by the operator during the emergency medical event.

14. The method of claim 13, wherein each entry includes multiple time stamps corresponding to initiation of a request to initiate the event, acknowledgment of the request to initiate the event, beginning of the performance of the event, completion of the performance of the event, and termination of the event due to a problem.

15. A non-transitory medium with instructions stored thereon that, when executed by a processor of a recording device, cause the recording device to perform operations comprising:
receiving input indicative of a request to initiate recording of an emergency medical event experienced by a patient and managed in an emergency event space;
causing display of an interface that includes (i) a representation of the patient and (ii) icons corresponding to different personnel and/or items that can be used to address the emergency medical event,
wherein the icons are positioned based on locations of the corresponding personnel and items in the emergency event space;
receiving a series of inputs indicative of drag-and-drop engagements with the icons over the course of the emergency medical event,
wherein each input corresponds to a drag-and-drop engagement in which an operator drags a corresponding icon toward the representation of the patient, the drag-and-drop engagement serving as an indication that an action involving a corresponding person or a corresponding item was observed by the operator or another individual and reported to the operator;
following each of the drag-and-drop engagements, prompting the operator to provide information regarding a corresponding action;
in response to a determination that information was not provided by the operator due to successive performances of multiple drag-and-drop engagements, providing feedback to the operator to provide the information;
adjusting visual appearances of the icons to reflect a number of times that each icon was involved in the drag-and-drop engagements, such that the visual appearance of each icon reflects involvement of the corresponding person or the corresponding item in the emergency medical event; and
generating, based on the series of inputs, a log of actions that serves as a non-transient record of the emergency medical event,
wherein each input is represented, in the log, with a separate entry that includes (i) an indication of the action and (ii) a time stamp that indicates when the operator completed that drag-and-drop engagement and when the action was performed.

16. The non-transitory medium of claim 15, wherein the operations further comprise:
comparing the log against a standard protocol that is representative of clinical algorithms developed by a standards organization for treatment of the emergency medical event; and
identifying differences discovered between the actions taken during the emergency medical event and the standard protocol.

17. The non-transitory medium of claim 15, wherein the actions taken for each of a set of emergency medical events are analyzed by algorithms and/or machine learning and/or artificial intelligence to identify variations in the performance of actions and protocols.

18. The non-transitory medium of claim 15, wherein each entry further includes (iii) information regarding a healthcare professional who performed the action.

19. The non-transitory medium of claim 15, wherein the interface includes roles of one or more healthcare professionals responsible for treating the patient, and wherein the operator is able to, through the interface, indicate which healthcare professional performed each action.

20. The non-transitory medium of claim 15, wherein the operations further comprise:
obtaining audio data generated over the course of the emergency medical event; and
generating, based on the audio data, a log of verbal interactions that serve as a non-transient record of the emergency medical event.

21. The non-transitory medium of claim 1, wherein the recording device is an augmented reality device or a virtual reality device worn by the operator.

22. The non-transitory medium of claim 15, wherein the icons are represented in an augmented reality environment that is representative of the emergency event space.

23. The non-transitory medium of claim 1, wherein the images are generated by a camera that is integrated into the recording device.

* * * * *